United States Patent [19]

Bombardelli et al.

[11] Patent Number: 5,750,562
[45] Date of Patent: May 12, 1998

[54] 10-DEACETYLBACCATINE III AND 10-DEACETYL 14β-HYDROXYBACCATINE III DERIVATIVES, A PROCESS FOR THE PREPARATION THEREOF AND PHARMACEUTICAL COMPOSITIONS CONTAINING THEM

[75] Inventors: Ezio Bombardelli; Paolo De Bellis; Bruno Gabetta, all of Milan, Italy

[73] Assignee: Indena S.p.A., Milan, Italy

[21] Appl. No.: 471,137

[22] Filed: Jun. 6, 1995

[30] Foreign Application Priority Data

Mar. 17, 1995 [IT] Italy ................... MI95A0533

[51] Int. Cl.$^6$ ................. A61K 31/335; C07D 305/14
[52] U.S. Cl. .................. 514/449; 549/510; 549/511
[58] Field of Search ................... 549/510, 54; 514/449

[56] References Cited

U.S. PATENT DOCUMENTS 5,264,591  11/1993  Bombardelli et al. ............ 549/214

FOREIGN PATENT DOCUMENTS 0 577 083 A1  6/1993  European Pat. Off. .

95/01969  1/1995  WIPO .

OTHER PUBLICATIONS

Gazetta Chimica Italiana, 124, 1994 The Chemistry and Occurence Of Taxane Derivatives. XIII, by Giovanni Appendino.

Heterocycles, vol. 38, No. 5, 1994 "Taxol Related diterpenes From The Roots Of Taxus Yunnanensis" by Zhang Hongjie et al.

Tetrahedron Letters, vol. 36, No. 18 pp. 3233–3236, 1995, "Synthesis of Modified Baccatins via an Oxidation-Reduction Protocol" by Giovanni Appendino et al.

*Primary Examiner*—Ba K. Trinh
*Attorney, Agent, or Firm*—Pennie & Edmonds LLP

[57] ABSTRACT

The present invention relates to novel derivatives of 10-deacetylbaccatine III and of 10-deacetyl-14 β-hydroxybaccatine III, having cytoxic and anti-tumoral activity. They are prepared starting from the so-called syntons or from other taxanes of natural origin, by selective oxidation of the hydroxyl in position 10 to keto function and subsequent esterification in position 13, if necessary, with isoserine chains variously substituted. The products of the invention can be administered by injection or orally, when suitably formulated.

11 Claims, No Drawings

10-DEACETYLBACCATINE III AND 10-DEACETYL 14β-HYDROXYBACCATINE III DERIVATIVES, A PROCESS FOR THE PREPARATION THEREOF AND PHARMACEUTICAL COMPOSITIONS CONTAINING THEM

TECHNICAL FIELD

The present invention relates to paclitaxel analogues and derivatives for use in applications in place of paclitaxel.

BACKGROUND ART

Paclitaxel (taxol), as it is already well-known, is a diterpenoid extracted from plants of the Taxus genus having anticancerogenic activity on different forms of human tumours. Its clinical use still involves some drawbacks due to the poor water solubility, which makes its administration complex, as well as to the onset of serious side-effects. Moreover, paclitaxel induces resistance quickly. Due to these reasons, research has been conducted for some years in attempts at synthesizing novel paclitaxel analogues which cause less adverse effects compared with the parent molecule.

SUMMARY OF THE INVENTION

The present invention relates to novel derivatives taxane skeleton endowed with a marked anti-tumoral activity. The novel derivatives have the general structure 1:

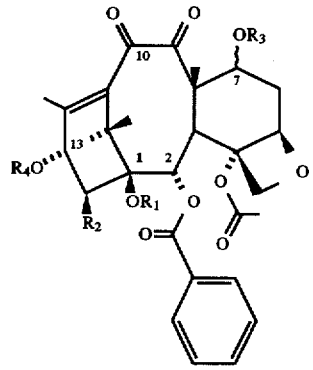

wherein $R_1$, and $R_2$ are hydrogen atoms, or $R_1$ is an hydrogen atom and R2 is an hydroxyl or an acetyloxy group, having izos carbonatoms or $OR_1$ and $R_2$ together form a cyclic carbonate group of formula:

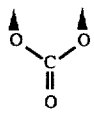

$R_3$, which can be α- o β-oriented, is an hydrogen atom or an alkylsilyl group having 1 to 12 carbon atoms in the alkyl moiety which can be straight chain or branched. $R_3$ is preferably triethylsilyl (TES); $R_4$ is hydrogen, or the residue

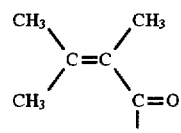

or an isoserine residue of formula A:

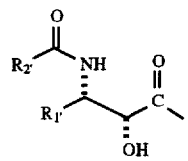

wherein $R_1'$ is a straight or branched alkyl or alkenyl group, containing one to five carbon atoms, or an aryl residue; $R_2'$ is a straight or branched alkyl or alkenyl group, containing one to five carbon atoms, or an aryl residue, or a tert-butoxy group.

DETAILED DESCRIPTION OF THE INVENTION

The novel derivatives of general formula (1) are prepared by semisynthesis, starting from the natural syntons 10-deacetylbaccatine III (2) and 10-deacetyl14β-hydroxybaccatine III(3). For this purpose, they are selectively oxidized in position 10 and then esterified in position 13 with a suitable acylating agent which allows to introduce the group $R_4$.

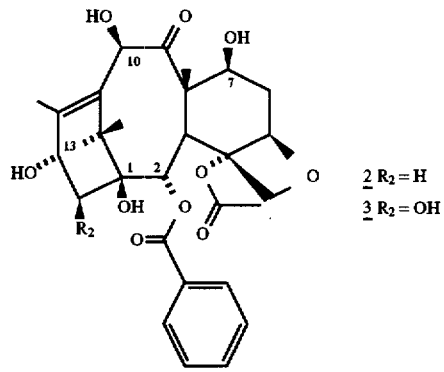

2 $R_2$ = H
3 $R_2$ = OH

When taxanes of natural or synthetic origin already containing the desired isoserine chain in position 13, the molecules of structure 1 can be obtained from said taxanes by selective oxidation in position 10. As it will be described hereinafter, the selective oxidation in position 10 of 2, 3 and of the taxanes already containing the isoserine chain in position 13, can be obtained by treatment with copper (II) salts. 10-Deacetylbaccatine III (2) and its 14β-hydroxy (3) analogous can be recovered from suitably selected vegetable material (see. Indena U.S. Pat. No. 5,264,591). However, and it is one of the objects of the present invention, it is possible to synthesize taxane syntons containing an oxygenated function in position 14, which are therefore useful for the preparation of compounds of structure 1, containing an oxygenated function in position 14, starting from 10-deacetylbaccatine III (2). In fact, it has surprisingly been found that, after protecting the hydroxyl in position 7 of compound 2 as a silyl ether, the oxidation to ketone of the carbon in 13 and the introduction of a β-oriented alcohol function on the carbon in 14 take place by treatment with manganese dioxide. After protection of the hydroxyls in 10 and 14, for example as acetates, by treatment with hydrides, the 13-keto function is reduced to 13α-hydroxy.

The process, which is schematized below, leads to the formation of synthon 4, useful for the preparation of compounds with structure 1.

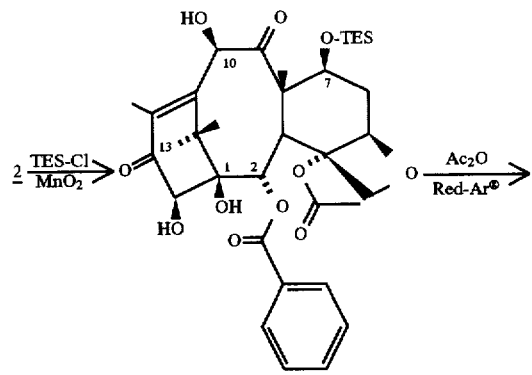

From synthon 4, after removing the protective groups with known methods described in literature, for example using hydrochloric acid to remove the silyl group and a base to remove the acetate groups, 10deacetyl-14β-hydroxybaccatine III (3) is obtained. Therefore, as mentioned, in order to prepare compounds of formula 1, 10-deacetylbaccatine III (2), 10deacetyl-14β-hydroxybaccatine III (3), natural or semisynthetic, or other taxanes having an hydroxyl function at 10 and already containing in position 13 the isoserine chain represented by the group $R_4$ must be available.

It has surprisingly been found that all these synthons, by treatment with copper (II) salts, preferably copper acetate, undergo a selective oxidation in position 10, without need for the protection of the other hydroxyl functions. For example, 10-deacetylbaccatine III (2), 10-deacetyl-14β-hydroxybaccatine III (3) and the natural taxane 10deacetylcephalomannine give the respective 10-keto derivatives 5–7 in yields from 75 to 85%. The oxidation generally requires protracted times (100–140 hours) and an excess of oxidizer and it is carried out at room temperature and in alcoholic solvent.

$\underline{5}$ $R_1 = R_2 = R_3 = R_4 = H$ $\underline{6}$ $R_1 = R_3 = R_4 = H; R_2 = OH$ $\underline{8}$ $R_1, R_2 = -CO-O; R_3 = R_4 = H$ $\underline{7}$ $R_1 = R_2 = R_3 = H; R_4 =$ (isobutenyl carbonyl group)

When, preparing the compound of formula 1 with, the presence of a cyclic carbonate group between the positions 1 and 14, synthon 3 is previously treated with phosgene in pyridine and the resulting carbonate is then oxidized in position 10 with copper (II) acetate, to give carbonate synton 8.

By treatment with bases, diketones 5–8 undergo an inversion in position 7, i.e. the hydroxyl in position 7 becomes α-oriented. Syntons 5, 6 and 8 or optionally their epimers in position 7, are therefore used for the preparation of taxanes of structure 1, after protection of the alcoholic functions present. The alcohol function in 13, contrary to the other hydroxyalcohol functions, is poorly reactive to silylation and therefore does not undergo derivatization.

For the esterification in position 13, the suitably activated isoserine chains are used, according to what reported in literature for the semisynthesis of paclitaxel and of its analogues (see. for example Eur. Pat. Appl. 400971, 1992; Fr. Dem. 86, 10400; E. Didier et al., Tetrahedron letters 35, 2349, 1994; E. Didier et al.; ibid 35, 3063, 1994). Preferably, isoserin chains are used in the activated forms of oxazolidinecarboxylic acids 9 a and 9 b.

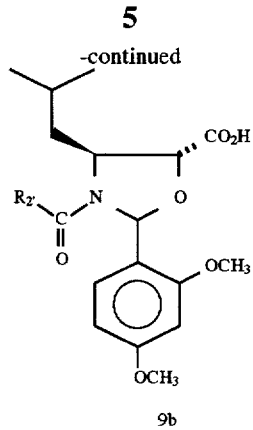

9b

In formulae 9a and 9b, R₁' and R₂' have the meaning described above. The esterification of the oxazolidinecarboxylic acids with the taxane syntons and the subsequent elimination of the protective groups are carried out as described in literature for the synthesis of paclitaxel and the analogues thereof.

Among the compounds of formula 1, compounds 10, 11 and 12 turned out to be particularly active. Compound 10 is 13-[(2R,3S)-3-ter-butoxycarbonylamino-2-hydroxy3-isobutyl-propanoyl]-10-deacetyl-10-dehydro-baccatine III. Therefore, referring to general formula 1, compound 10 has: $R_1 = R_2 = H$, $OR_3 = -\beta\text{-OH}$, $R_1' = \text{iso-But}$, $R_2' = \text{t-BuO}$. Compound 11 is 13=[(2R,3S)-3-ter-butoxycarbonylamino-2-hydroxy-3-isobutyl-propanoyl]-10-dehydro-10-deacetyl-14β-hydroxy-baccatine III 1,14-carbonate. Therefore 11, referring to general formula 1, has $R_1, R_2 = -CO-O$, $OR_3 = \beta\text{-OH}$, $R_1' = \text{iso-But}$, $R_2' = \text{t-BuO}$.

Compound 12 is 13-[(2R,3S)-3-caproylamino-2-hydroxy-3-isobutyl-propanoyl]-10-dehydro-10-deacetyl 14β-hydroxy-baccatine III 1,14-carbonate. Therefore 12, referring to general formula 1, has $R_1, R_2 = -CO-O$, $OR_3 = -B-OH$, $R_1' = \text{iso-But}$, $R_2' = C_5H_{11}$.

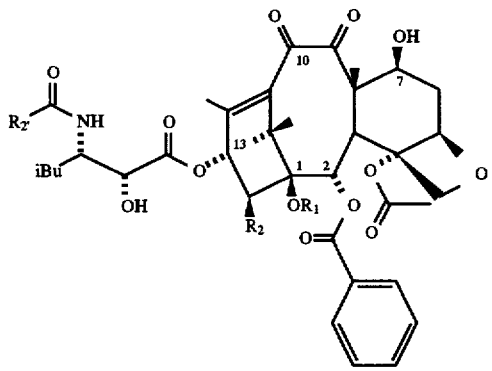

10 R₁ = R₂ = H, R₂' = t-butoxy
11 R₁, R₂ = CO—O, R₂' = t-butoxy
12 R₁, R₂ = CO—O, R₂' = C₅H₁₁

The cytotoxicity data of the compounds 10 and 11 compared with those of paclitaxel are reported in Table 1.

TABLE 1

IC₅₀s of compounds 10, 11 and paclitaxel on 6 human tumour cell lines.

| Cell line | Exposition time (h) | IC₅₀ (nM) Paclitaxel | 10 | 11 |
|---|---|---|---|---|
| L1210 (murine leukemia) | 48 | 7.0 ± 3.0 | 0.6 ± 0.1 | 2.0 ± 0.1 |
| A121 (human ovarian) | 72 | 3.7 ± 0.3 | 0.8 ± 0.3 | 1.6 ± 0.2 |
| A549 (human NSCLC) | 72 | 5.4 ± 0.5 | 1.9 ± 0.3 | 2.1 ± 0.3 |
| HT-29 (human colon) | 72 | 6.0 ± 0.6 | 0.4 ± 0.1 | 0.6 ± 0.4 |
| MCF7 (human breast) | 72 | 4.3 ± 0.1 | 1.2 ± 0.2 | 0.8 ± 0.2 |
| MCF7-ADR (resistant) | 72 | 395 ± 8.7 | 13 ± 2.2 | 28 ± 6.2 |

Standard conditions: basal medium - RPMI 1640 + 20 mM HEPES + 2 mM L-Glutamine.

Compounds of formula 1 show surprising advantages compared with paclitaxel on cell lines resistant to other anti-tumoral substances, such as adriamycin or cis-platinum. The differences between paclitaxel and these products are even more evident in in vivo models, such as athymic nude mouse with human tumor implant. Moreover, it has been found that the compounds of the invention in which R'₂ is an alkyl or alkenyl group are surprisingly devoid of cardiotoxic activity, contrary to taxol and the known derivatives thereof, and therefore they can advantageously be used in the treatment of tumors in cardiopathic patients who cannot be treated with taxol and its known derivatives. The products object of the invention can be incorporated in suitable pharmaceutical formulations for the administration of the products both parenterally and orally. For the intravenous administration, mixtures of Chremoform L and ethanol, polysorbates or liposomial preparations prepared with natural or synthetic phosphatidylcholine or mixtures of natural phospholipids in the presence of cholesterol are mainly used.

The EXAMPLES following examples further illustrate the invention.

Example 1

Preparation of 10-deacetyl-10dehydrobaccatine III (5). 10 g of 10-deacetylbaccatine III (2), (isolated as described by G. Chauviere et al., C. R. Acad. Sci. Ser. II 293, 591, 1981) are suspended in 350 ml of methanol and mixed with 65 g of Cu(OAc)₂. The suspension is stirred at room temperature for 120 h. The salts are filtered off and the solution is chromatographed on 100 g of silica gel eluting with a hexane/ethyl acetate 6:4 mixture. Upon crystallization from ligroin, 9.5 g of (5) are obtained. M+a m/z 542.

Example 2

Preparation of 10-deacetyl-10-dehydro-14βhydroxybaccatine III 1,14-carbonate (8). 10 g of 10-deacetyl-143-hydroxybaccatine III (3), isolated as described by G. Appendino et al., J. Chem. Soc. Perkin Trans I, 2925, 1992, are dissolved in 50 ml of anhydrous pyridine and treated for one hour with 1.5 eq. of 5% phosgene in toluene at −10° C. The reaction mixture is poured onto ice and the aqueous suspension is extracted with ethyl acetate, washing thoroughly the organic phase with diluted HCl. After drying over Na₂SO₄ the organic phase is concentrated to dryness. 9 g of 1,14-carbonate are obtained, which are suspended in 350 ml of methanol and treated with 50 g of Cu(OAc)₂ under stirring at room temperature for 120 h. The suspension is filtered and the solution is evaporated to dryness. The residue is chromatographed on 100 g of silica

Example 3
Preparation of 13-[(2R,3S)-3-ter-butoxycarbonylamino-2-hydroxy-3-isobutyl-propanoyl]10deacetyl-10-dehydrobaccatine III (10)

A solution of 300 mg (1.84 mmol) of 7-Otriethylsilyl-10-deacetyl-10-dehydrobaccatine, III, obtained from compound (5) (Example 1) by silylatio in position 7 according to the method described by J. Denis et al., J. Am. Chem. Soc Vol.100 page 5917, 1988 in 60 ml of toluene is mixed with 500 mg of (4S, 5R)-N-(ter-butoxycarbonyl)-2,2-dimethyl-4-isobutyl-5-oxazolidineecar boxylic acid, 240 mg of dicyclohexylcarbodiimide (1.2 eq.) and 24 mg of N,N-dimethylaminopyridine (0.2 eq). The reaction mixture is kept at 80° C. for 2 hours, then is filtered and washed with water; the organic phase is concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel eluting with acetone/hexane 4:6. 350 mg of (10) are obtained. $M^{+a\ m/z}$ 785.

Example 4
Preparation of 13-[(2R,3S)-3-tertbutoxycarbonyl-amino-2-hydroxy-3-isobutyl-propanoyl]10deacetyl-10-dehydro-143-hydroxybaccatine III 1,14carbonate (11).

0.5 g of 7-o-triethylsilyl-10-deacetyl-10-dehydro-14β-hydroxybaccatine III 1,14-carbonate, obtained from compound (8) (Example 2) by silylation in position 7 according to what reported by J. Denis et al., J. Am. Soc. 100. 5917. 1988. are dissolved in 60 ml of toluene. The solution is mixed with 800 mg of (4S,5R)N-(tert-butoxycarbonyl)-2,2-dimethyl-4-isobutyl-5- oxazolidinee-carboxylic acid, 400 mg of cyclohexylcarbodiimide and 40 mg of N,N-dimethylaminopyridine. The reaction mixture is kept at 80°0 C. for two hours, then is filtered and washed with water and the organic phase is concentrated to dryness. The residue is treated with methanol containing 0.1% of $H_2SO_4$ at 10° C. The methanol solution is diluted with water and the product is extracted with ethyl acetate; the organic phase is concentrated to dryness and the residue is chromatographed on silica gel, eluting with acetone/hexane 4:6. 580 mg of (11) are obtained, $M^+a$ m/z 827.

Example 5
Preparation of 10-deacetyl-10-dehydro-14β-hydroxybaccatine III (6).

10 g of 10-deacetyl-14β-hydroxybaccatine III (3) are suspended in 350 ml of methanol and mixed with 65 g of $Cu(OAc)_2$. The suspension is kept under stirring at room temperature for 120 h. The salts are filtered off, the solution is evaporated to dryness and the residue is chromatographed on 100 g of silica gel eluting with a hexane/ethyl acetate 6:4 mixture. Upon crystallization from ligroin, 9.3 g of (6) are obtained, $M^+a$ m/z 558.

Example 6
Preparation of 10-deacetyl-10-dehydrocephalomannine (7).

0.4 g of 10-deacetylcephalomannine (J. L. Laughlin et al., J. Nat. Prod. 44, 312, 1981) are dissolved in 5 ml of MeOH and mixed with 600 mg of $Cu(OAc)_2$. The reaction mixture is left under stirring for 54 hours at room temperature. After eliminazione of the salts for filtration, the solution The salts are filtered off, the solution is evaporated to dryness and chromatographed on silica gel (10 g) using a hexane-acetate d'ethyl 1:1 mixture as eluent. 220 mg of (7) are obtained, $M^+a$ m/z 829.

Example 7
Preparation of 7-triethylsilyl-14βhydroxybaccatine III (4)

500 mg of 7-triethylsilyl-10-deacetylbaccatine III, prepared according to the method by J. Denis et al., J. Am. Chem. Soc. Vol. 100 page 5917, 1988 are dissolved in 15 ml of a ethyl acetate-methylene chloride 9:1 mixture. The solution is mixed with 10 g of $MnO_2$ leaving the suspension at room temperature under stirring for 24 hours. After filtration, the solution is evaporated to dryness and the residue is chromatographed on silica gel (20 g) eluting with a hexane-ethyl acetate 8:2 mixture. 310 mg of 7triethylsilyl-10-deacetyl-13-dehydro-14βhydroxybaccatine III are obtained ($M^+a$ m/z 672).

300 mg of this product are dissolved in 2 ml of pyridine. The solution is mixed with 910 mg of $Ac_2O$. After 16 hours the reaction mixture is poured onto ice and then extracted with ethyl acetate. The organic phase is washed with diluted HCl and then with water to neutrality. After evaporation of the solvent, the residue is crystallized from ether (220 mg, $M^+a$ m/z 756). The solid is dissolved in 10 ml of anhydrous THF; the solution is added with 160 μl of sodium bis (2methoxy-ethoxy)aluminum hydride (65% solution). After about 10 minutes, 10 ml of a $NH_4Cl$ saturated solution are added, extracting then with ethyl acetate. The organic phase is evaporated to dryness. The residue is purified on silica gel (15 g) eluting with a hexaneethyl acetate 7:3 mixture. 80 mg of (4) are obtained, $M^+a$ 716.

Example 8
Preparation of (4S,5R)-N-caproyl-2-(2,4dimethoxyphenyl)-4-isobutyl-5-oxazolidinee carboxylic acid methyl ester.

5 g of N-caproyl-β-isobutyl-isoserine methyl ester are dissolved in 200 ml of a mixture of anhydrous THF and benzene and the solution is treated with 2 equivalents of 2,4-dimethoxy benzaldehyde dimethyl acetal in the presence of 120 mg of pyridinium ptoluenesulfonate. The solution is refluxed for 1 hour. The solvent is distilled and the residue is chromatographed on silica gel eluting the main compound with a ethyl acetate/hexane 8:2 mixture. After removing under vacuum the solvent from the fraction containing the desidered isomer, the residue is crystallized from hexane/isopropyl ether. 2.5 g of a compound having m.p. 98° C. are obtained.

Example 9
Preparation of (4S,5R)-N-caproyl-2-(2,4dimethoxyphenyl)-4-isobutyl-5 oxazolidine carboxylic acid 2 g of the compound of Example 8 are suspended in 50 ml of a mixture of methanol aqueous (8:2) containing 5 g of $K_2CO_3$. The reaction mixture is left under stirring until complete dissolution of the isoserine derivative. The reaction mixture is carefully acidified to pH 5. with stirring, in the presence of ethyl acetate. The aqueous phase is discarded, whereas the organic one is dried over sodium sulfate and concentrated to dryness at low temperature under vacuum. The residue is dissolved in a toluene/methylene chloride mixture and it is ready for the reaction with the selected taxanes.

Example 10
Preparation of 13-[(2R,3S)-3-caproylamino2-hydroxy-3-isobutyl-propanoyl]-10-dehydro-10-deacetyl 14β-hydroxybaccatine III 1,14-carbonate (12) 5 g of 1,14-carbonate-7-TES-10-dehydro-baccatine III are dissolved in 100 ml of a mixture of toluene and methylene chloride in a 8,2 ratio, together with 6 g of (4S,5R)-N-caproyl-2-(2,4-dimethoxyphenyl)-4-isobutyl-5oxazolidine carboxylic acid. The reaction mixture is added with 500 mg of 4-dimethylaminopyridine and 2.5 g of 1,3-dicyclohexylcarbodiimide, then heated for 2 hours under mild reflux until the reagents disappear. The compounds insoluble in the medium are filtered off and the solution is concentrated to dryness. The residue is taken up with 50 ml of methanol/HCl (0.01%) and the reaction mixture is left at room temperature for 1 hour. The solution is alkalinized to pH 5 and concentrated to dryness in the vacuum. The residue is chromatographed on a silica gel column eluting with a methylene chloride/methanol 98:2 mixture. Upon crystallization from ethyl acetate, 1.2 g of compound (12) are obtained.

Example 11
Solution of compound (10) for parenteral administration

| Compound 10 | 2 mg |
|---|---|
| Cremophor EL | 175 mg |
| Absolute alcohol | q.s. to 0.4 ml. |

Example 12
Solution of compound (11) for parenteral administration

| Compound 11 | 2 mg |
|---|---|
| Cremophor EL | 175 mg |
| Absolute alcohol | q.s. to 0.4 ml. |

Example 13
Tablets containing compound (10)

| Compound 10 | 10 mg |
|---|---|
| Cross-linked sodium carboxymethyl cellulose | 15 mg |
| Lactose (spray dried) | 41.5 mg |
| Microcrystalline cellulose | 40 mg |
| Colloidal silicon dioxide | 0.5 mg |
| Magnesium stearate | 1 mg. |

Example 14
Tablets containing compound (11)

| Compound 11 | 10 mg |
|---|---|
| Cross-linked sodium carboxymethyl cellulose | 15 mg |
| Lactose (spray dried) | 41.5 mg |
| Microcrystalline cellulose | 40 mg |
| Colloidal silicon dioxide | 0.5 mg |
| Magnesium stearate | 1 mg. |

Example 15
Capsules containing compound (10)

| Compound 10 | 10 mg |
|---|---|
| Lactose (spray dried) | 30 mg |
| Microcrystalline cellulose | 48.5 mg |
| Pre-gelatinized starch | 10 mg |
| Magnesium stearate | 1 mg |
| Colloidal silicon dioxide | 0.5 mg. |

Example 16
Capsules containing compound (11)

| Compound 11 | 10 mg |
|---|---|
| Lactose (spray dried) | 30 mg |
| Microcrystalline cellulose | 48.5 mg |
| Pre-gelatinized starch | 10 mg |
| Magnesium stearate | 1 mg |
| Colloidal silicon dioxide | 0.5 mg. |

We claim:
1. 10-Deacetylbaccatine III and 10-deacetyl-14β-hydroxybaccatine III derivatives of formula (1)

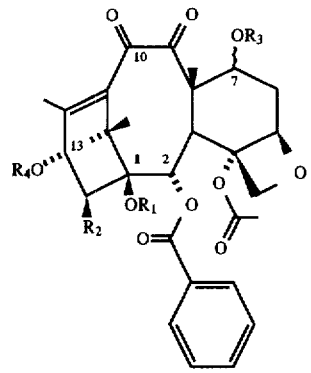

wherein $R_1$ and $R_2$ are hydrogen atoms, or $R_1$ is a hydrogen atom and $R_2$ is a hydroxyl or an acetyloxy group, or $OR_1$ and $R_2$ together form a cyclic carbonate group of formula:

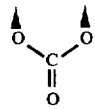

$R_3$, which can be α- or β-oriented, is a hydrogen atom or an alkylsilyl group having 1 to 5 carbon atoms, $R_4$ is hydrogen, or the residue

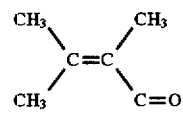

or an isoserine residue of formula A:

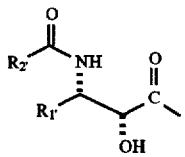

wherein $R_1$, is a straight or branched alkyl or alkenyl group, containing one to five carbon atoms, or an aryl residue; $R_2$, is a straight or branched alkyl or alkenyl group, containing one to five carbon atoms, or an aryl residue, or a tert-butoxy group, provided that when $R_1$, is an aryl group and $R_2$ is a tert-butoxy group, $R_1$, $R_2$ and $R_3$ are not all hydrogen atoms.

2. A compound according to claim 1, selected from the group consisting of:

10-deacetyl-10-dehydrobaccatine III;

10-deacetyl-10-dehydro-14β-hydroxybaccatine III;

10-deacetyl-10-dehydrocephalomannine;

10-deacetyl-10-dehydro-14β-hydroxybaccatine III 1,14-carbonate;

13-[(2R,3S)-3-tert-butoxycarbonylamino-2-hydroxy3-isobutyl-propanoyl]10-deacetyl-10-dehydrobac catine III;

13-[(2R,3S)-3-tert-butoxycarbonylamino-2-hydroxy3-isobutyl-propanoyl]10-deacetyl-10-dehydro-14β-hydroxybaccatine III 1,14-carbonate;and 13-[(2R,3S)-3-caproylamino-2-hydroxy-3-isobutylpropanoyl]-10-dehydro-10-deacetyl-14β-hydroxy baccatine III 1,14-carbonate.

3. Pharmaceutical compositions containing as the active ingredient one or more compounds of formula 1 according to claim 1, with $R_3$ =H and a Pharmaccutically acceptable carrier.

4. Pharmaceutical compositions according to claim 3, which can be administered parenterally or orally, provides a series of compounds which achieve that goal.

5. A compound according to claim 1 wherein $R_3$ is a triethylsilyl group.

6. A compound according to claim 1 wherein $R_3$ is hydrogen.

7. A compound according to claim 1 wherein $R_2$ is an alkyl or alkenyl group.

8. A compound according to claim 1 specifically as

13-[(2R,3S)-3-tert-butoxycarbonylamino-2-hydroxy-3-isobutylpropanoyl]-10-deacetyl-10-dehydrobaccatine III;

13-[(2R,3S)-3-tert-butoxycarbonylamino-2-hydroxy-3-isobutylpropanoyl]-10-deacetyl-14β-hydroxybaccatine III 1,14- III 1,14PENY2-378076.2 carbonate; or 13-[(2R,3S)-3-benzoylamino-2-hydroxy-3-phenylpropanoyl]-10-deacetyl-10-dehydrobaccatine III.

9. A method of treatment of a tumor in a cardiopathic patient, which comprises administering to said patient one of the compounds of claim 8.

10. A method of treatment of a tumor in a cardiopathic patient, which comprises administering to said patient 10-deacetylbaccatine III and 10-deacetyl-14β-hydroxybaccatine III derivatives of formula (1)

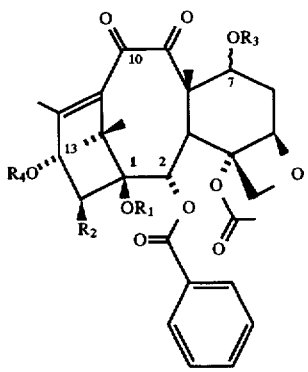

I wherein $R_1$ and $R_2$ are hydrogen atoms, or $R_1$ is a hydrogen atom and $R_2$ is a hydroxyl or an acetyloxy group, or $OR_1$ and $R_2$ together form a cyclic carbonate group of formula:

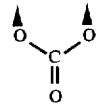

$R_3$, which can be α- or β-oriented, is a hydrogen atom or an alkylsilyl group having one to five carbon atoms, $R_4$ is hydrogen, or the residue

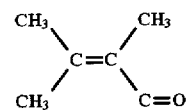

or an isoserine residue of formula A:

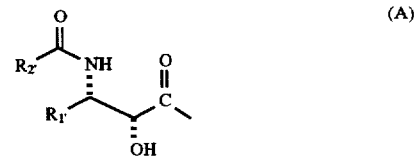

(A)

wherein $R_1$ is a straight or branched alkyl or alkenyl group, containing one to five carbon atoms, or an aryl residue, and $R_2$, is a straight or branched alkyl or alkenyl group, containing one to five carbon atoms, or an aryl residue, or a -tert-butoxy group; provided that when $R_1$ is an aryl group and $R_2$ is a tert-butoxy group, $R_1$, $R_2$, and $R_3$ are not all hydrogen atoms.

11. The method of treatment according to claim 10, wherein $R_2$ is an alkyl or alkenyl group.

* * * * *

UNITED STATES PATENT AND TRADEMARK OFFICE
CERTIFICATE OF CORRECTION

PATENT NO. : 5,750,562

DATED : May 12, 1998

INVENTORS : Bombardelli et al.

It is certified that error appears in the above-identified patent and that said Letters Patent is hereby corrected as shown below:

Column 1, line 27: after "ecule." insert --The present invention provides a series of compounds which achieve that goal.--.

Column 1, line 33: after "derivatives" insert --of taxol which have a--.

Column 1, line 53: change "R2" to --$R_2$-- and after "group" insert --having 1 to 5 carbon atoms--.

Column 1, line 54: delete "having izos carbonatoms".

Column 5, line 18: change "$R_1$'and $R_2$'have" to --$R_{1'}$ and $R_{2'}$ have--.

Column 5, line 28: change "-hydroxy3-" to ---hydroxy-3---.

Column 6, lines 39-40: delete "The EXAMPLES following examples further illustrate the invention." and insert the heading --EXAMPLES--.

Column 6, between lines 40 and 42: insert --The following examples further illustrate the invention--.

Column 6, line 62: after "$Na_2SO_4$" insert --,--.

Column 7, line 10: change "silyltio" to ---silylation---

UNITED STATES PATENT AND TRADEMARK OFFICE
CERTIFICATE OF CORRECTION

PATENT NO. : 5750562
DATED : May 12, 1998
INVENTOR(S) : Bombardelli et al.

It is certified that error appears in the above-identified patent and that said Letters Patent is hereby corrected as shown below:

Column 7, line 11: change "Soc" to --Soc.--.

Column 7, line 32: change "Soc. 100. 5917." to --Soc., Vol. 100, page 5917,--.

Column 8, line 5: change "Soc. Vol. 100 page 5917, 1988 are" to --Soc., Vol. 100, page 5917, 1988, are--.

Column 10, line 52: change "$R_1$," to --$R_{1'}$--.

Column 10, line 53: change "$R_2$," to --$R_{2'}$--.

Column 10, line 56: change "$R_1$," to --$R_{1'}$-- and change "$R_2$is" to --$R_{2'}$ is--.

Column 10, line 65: change "-hydroxy3-" to ---hydroxy-3---.

Column 10, line 66: change "-dehydrobac catine" to ---dehydrobaccatine--.

Column 11, line 1: change "-hydroxy3-" to ---hydroxy-3---.

Column 11, line 3: change "-carbonate;and" to ---carbonate; and--.

Column 11, line 9: change "Pharmaccutically" to --pharmaceutically--.

Column 11, lines 12-13: delete "provides a series of compounds which achieve that goal."

Column 11, line 24: change "13" to --13--.

Column 11, line 26: delete "PENY2-378076.2".

Column 11, line 26: "III 1,14" should be deleted (second occurence)

UNITED STATES PATENT AND TRADEMARK OFFICE
CERTIFICATE OF CORRECTION

PATENT NO. : 5750562
DATED : May 12, 1998
INVENTOR(S) : Bombardelli et al.

It is certified that error appears in the above-identified patent and that said Letters Patent is hereby corrected as shown below:

Column 12, line 38: change "$R_1$is" to --$R_{1'}$ is--.

Column 12, line 40: change "$R_2$," to --$R_{2'}$--.

Column 12, line 42: change "-tert-butoxy" to --tert-butoxy-- and change "$R_1$is" to --$R_{1'}$ is--.

Column 12, line 43: "$R_2$is" to --$R_{2'}$ is--.

Signed and Sealed this

Eighth Day of September, 1998

Attest:

BRUCE LEHMAN

Attesting Officer

Commissioner of Patents and Trademarks